US00PP28547P2

(12) United States Plant Patent
Gerdts et al.

(10) Patent No.: US PP28,547 P2
(45) Date of Patent: Oct. 24, 2017

(54) PEACH TREE NAMED 'BURPEACHTHIRTYEIGHT'

(50) Latin Name: *Prunus persica*
Varietal Denomination: Burpeachthirtyeight

(71) Applicants: Timothy J. Gerdts, Kingsburg, CA (US); John K. Slaughter, Fresno, CA (US)

(72) Inventors: Timothy J. Gerdts, Kingsburg, CA (US); John K. Slaughter, Fresno, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 9 days.

(21) Appl. No.: 14/999,028

(22) Filed: Mar. 21, 2016

(51) Int. Cl.
*A01H 5/08* (2006.01)

(52) U.S. Cl.
USPC ..... Plt./197

(58) Field of Classification Search
USPC ..... Plt./197
See application file for complete search history.

*Primary Examiner* — Susan McCormick Ewoldt
(74) *Attorney, Agent, or Firm* — Randall Danskin P.S.

(57) ABSTRACT

A new and distinct variety of peach tree (*Prunus persica*), which is denominated varietally as 'Burpeachthirtyeight', and which produces an attractively colored yellow fleshed, clingstone peach which is mature for harvesting and shipment approximately September 18 to September 23 under the ecological conditions prevailing in the San Joaquin Valley of central California.

1 Drawing Sheet

Botanical designation: The present invention relates to a new, novel, and distinct variety of peach tree, *Prunus persica.*

Varietal denomination: 'Burpeachthirtyeight'.

BACKGROUND OF THE NEW VARIETY

The present variety of peach tree resulted from an ongoing program of fruit nut rootstock tree breeding. The purpose of this program is to improve the commercial quality of deciduous fruit and nut varieties, and rootstocks, by creating and releasing promising selections of *Prunus, Malus, Punica* and *Juglans* species. To this end we make both controlled, and hybrid cross pollinations, each year, in order to produce seedling populations from which improved progenies are evaluated and selected.

The seedling, 'Burpeachthirtyeight' was originated by us, and selected from a population of seedlings growing in our experimental orchards which are located near Fowler, Calif. The seedlings, grown on their own roots, were derived from planting seed of the 'Summer Lady' Peach Tree (U.S. Plant Pat. No. 5,865), a commercially released, yellow-fleshed peach. The pollen parent was an unnamed, late ripening, clingstone peach selection (un-patented). Fruit was collected from the female parent, and seeds were then extracted. After a period of stratification, the seeds were placed in our greenhouse, by population, and then field planted for tree establishment, and ultimately to exhibit fruit for further evaluation. One yellow fleshed peach seedling, which is the present variety, exhibited especially desirable characteristics, and was then designated as 'J26.080'. This seedling was marked for subsequent observation. After the 2004 fruiting season, the new variety of peach tree was selected for advanced evaluation, and repropagation. In comparison to its parents, the new variety is both a later ripening variety (approximately 6 weeks), and further displays fruit having a clingstone characteristic. Both of the aforementioned characteristics are different than the traits of female parent, 'Summer Lady' Peach Tree (U.S. Plant Pat. No. 5,865). Additionally, the new variety of peach tree produces fruit which are more rounded in shape, flavorful and exhibits more external reddish blush than its' unnamed, late ripening clingstone male parent.

ASEXUAL REPRODUCTION

Asexual reproduction of this new and distinct variety of peach tree was accomplished by budding the new peach tree onto 'Nemaguard' Rootstock (un-patented). This was performed, by us, in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF VARIETY

'Burpeachthirtyeight' is a new and distinct variety of peach tree, which is considered of relatively large size, and which further has a vigorous growth characteristic. This new tree is also a regular, and productive bearer of relatively large, firm, yellow-fleshed, acidic, clingstone fruit which have a very good flavor, and eating qualities. This new peach tree has a medium chilling requirement of approximately 650 hours, and further produces relatively uniformly sized fruit throughout the tree's canopy. In addition to the foregoing, the fruit of the new peach tree also appears to have good handling and shipping qualities. The 'Burpeachthirtyeight' peach tree bears fruit which are typically ripe for commercial harvesting and shipment on approximately September 18 to September 23 under the ecological conditions prevailing in the San Joaquin Valley of central California. In relative comparison to the 'Autumn Rose' peach tree (U.S. Pat. No. 7,990), which is the closest known commercial variety, the new variety of peach tree bears fruit that ripens 5-7, or more days, earlier. Further, the current variety produces fruit which exhibit a more rounded shape especially at the apex. Additionally, the current variety produces fruit which exhibit a higher percentage of reddish blush on the surface of the fruit. Moreover, the fruit of the new variety is a true clingstone fruit which is different from the fruit produced by the 'Autumn Rose' peach tree, and which produces a full freestone-fruit.

BRIEF DESCRIPTION OF THE DRAWING

The accompanying drawing, which is provided, is a color photograph of the new peach variety.

The photograph depicts two whole mature fruit viewed from both the apical, and basal aspects.

Figure 80:
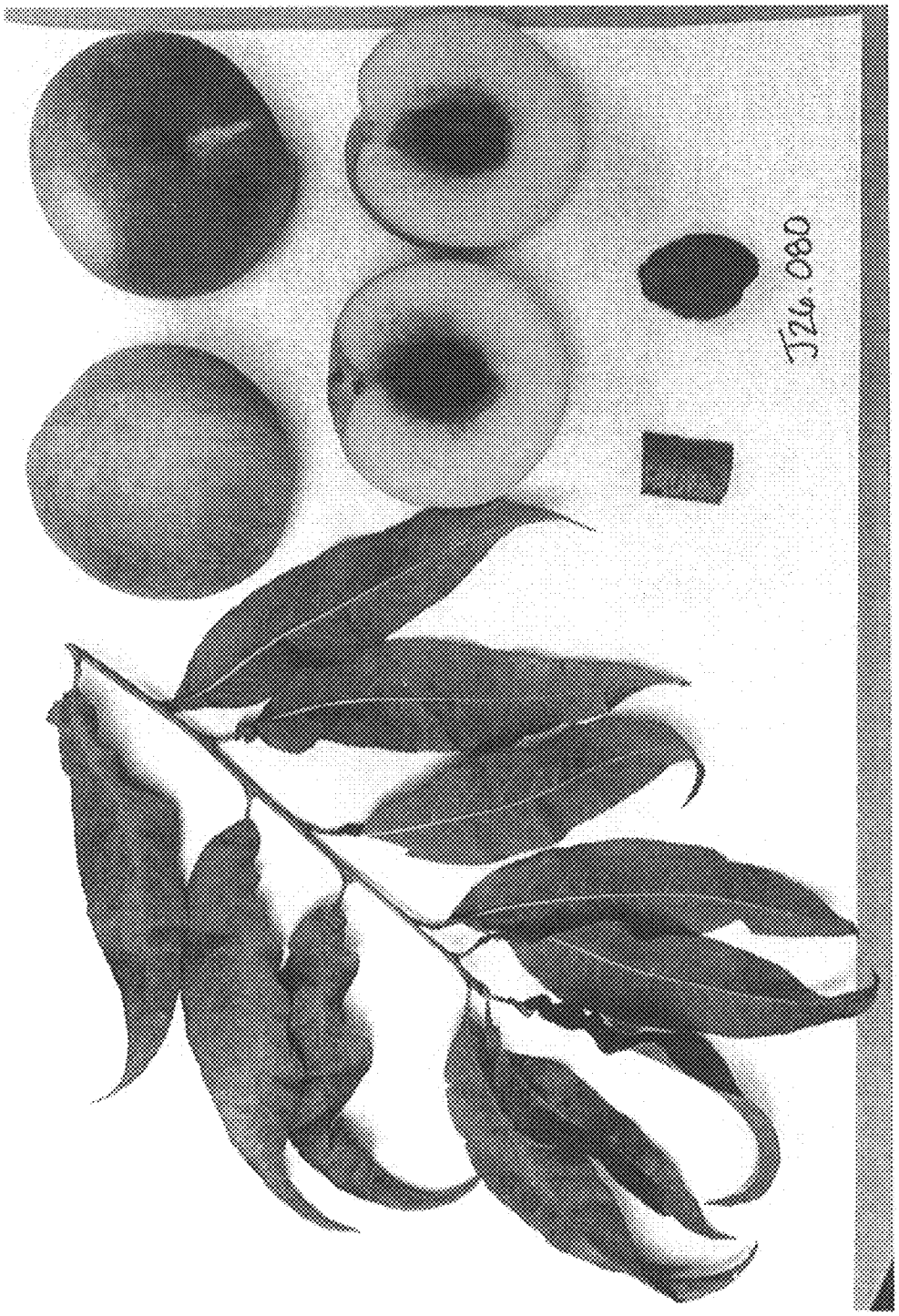

Additionally one mature fruit is shown bisected in the sutural plane, and which displays the flesh color, and the exposed stone characteristics thereof.

A small piece of bark from a mature tree is also shown in the drawing, as well as a stone that has had the flesh removed to exhibit the general shape and surface texture of the stone.

A vegetative shoot of current season's growth is also shown.

The external coloration of the fruit as illustrated in the photograph is sufficiently matured for harvesting and shipment. The colors in this photograph are as nearly true as is reasonably possible in a color representation of this type. Due to chemical development, processing and printing, the leaves and fruit depicted in this photograph may, or may not, be accurate when compared to the actual specimen. For this reason, future color references should be made to the color plates (Royal Horticultural Society Colour Chart of The Royal Horticultural Society of London, Fourth Edition, 2001) and descriptions provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will, in the future, display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of peach tree, the following has been observed during the 8th fruiting season, and under the ecological conditions prevailing at the orchards of the assignee which are located near the town of Fowler, county of Fresno, state of California. All major color code designations are by reference to The R.H.S. Colour Chart (Fourth Edition, 2001), and which is provided by The Royal Horticultural Society of Great Britain. Common color names are also occasionally used.

TREE

Tree size: Generally considered medium to medium-large in its growth pattern as compared to other common commercial peach cultivars ripening in the late season of maturity. The tree of the present variety was pruned to a height of approximately 260.0 cm. to about 300.0 cm. at commercial maturity.

Tree width: Approximately 285.0 cm.

Tree vigor: Considered moderately vigorous. The present peach tree variety grew from about 160.0 cm. to about 170.0 cm., in height, during the first growing season. The new variety was pruned to a height of approximately 150.0 cm. during the first dormant season, and primary scaffolds were then selected for the desired tree structure.

Tree productivity: Productive. Fruit set varies from more than the desired crop load, to levels higher than desired amounts, when the new variety is grown in a suitable horticultural zone, and under appropriate commercial nursery conditions. The fruit set is typically spaced by thinning to develop the remaining fruit into the desired market-sized fruit. The number of the fruit set varies with the prevailing climatic conditions, and the horticultural practices employed.

Fruit bearing: Regular. Fruit set has been more than adequate during the previous years of observation, and thinning was necessary during the past 8 years on both the originally discovered seedling, and on subsequent asexually reproduced trees.

Tree form: Upright, and pruned into a vase shape.

Density: Considered moderately dense. It has been discovered that pruning the branches from the center of the tree to obtain a resulting vase shape allows for enhanced air movement, and appropriate amounts of sunlight to improve fruit color, and renewal of fruiting wood throughout the tree.

Hardiness: The present tree was grown and evaluated in USDA Hardiness Zone 9. The calculated winter chilling requirements of the new tree is approximately 650 hours at a temperature below 7.0 degrees C. The present variety appears to be hardy under typical central San Joaquin Valley climatic conditions.

TRUNK

Diameter: Approximately 18.5 cm in diameter when measured at a distance of approximately 15.24 cm. above the soil level. This measurement was taken at the end of the 8th growing season.

Bark texture: Considered moderately rough, with folds of papery scarfskin being present. Since bark development, and coloration change with advancing tree age, this characteristic varies with the tree vigor, age and regional environmental conditions. Therefore, this is not a dependable descriptor of the new variety.

Trunk lenticels: Flat, oval lenticels are present but are not considered abundant. The lenticels range in size from approximately 3.0 millimeters, to about 5.0 mm. in width, and between about 2.0 and about 3.0 millimeters, in height. The development and size of the trunk lenticels can be influenced, to some degree, by the ambient growing conditions, and are not, necessarily, a dependable characteristic of this variety. As trees of this variety mature, lenticels are present, but they are generally covered by increasing layers of cork (mature bark), and therefore become less apparent.

Trunk lenticel color: Considered an orange brown, (RHS Greyed-Orange Group N167 A).

Trunk bark color: Variable, but it is generally considered to be a greyed-brown, (RHS Grey-Brown Group N200 B). This bark description was taken from trees in their eighth leaf.

BRANCHES

Size: Considered medium large for the variety.

Branch diameter: Average as compared to other peach tree varieties. The branches typically have a diameter of about 12.0 centimeters when measured during the 8th year after grafting.

Branch surface texture: Average, and appearing furrowed on wood which is several years old.

Flowering shoot thickness: Approximately 6.0-10.0 millimeters.

Branch crotch angle: The crotch angle of primary branches are considered variable, and are usually observed growing at an angle of about 48 to about 55 degrees when measured from a horizontal plane. This particular growth characteristic can be influenced, to some degree, by tree vigor, rootstock and other horticultural conditions.

Current season shoots:

*Surface texture.*—Substantially glabrous.

Internode length: Approximately 24.0 mm. The internode length can be somewhat variable due to tree growth patterns which are influenced, at least in part, by the current orchard growing conditions.

Color of mature branches: Grey-brown, (RHS Greyed-Brown Group N199 B).

Current season's shoots:

*Color.*—Medium green, (RHS Green Group 143 B). The color of new shoot tips is considered a bright and shiny green (RHS Yellow-Green Group 146 C). It should be understood that the vegetative shoot color can be significantly influenced by plant nutrition, irrigation practices, and exposure to sunlight, and therefore should not be considered a consistent botanical characteristic of this new variety.

LEAVES

Size: Considered medium-large for the species. The leaf measurements, as noted below, have been taken from vigorous, upright, current-season growth, at approximately mid-shoot. It should be understood that the leaf size is often influenced by prevailing growing conditions, quality of sunlight, and the location of the leaf within the tree canopy. For this reason, leaf sizes can vary significantly based upon the ambient and other cultural factors listed, above, and are not typically considered a dependable botanical descriptor.

Leaf length: Approximately 155.0 to about 170.0 millimeters.

Leaf width: Approximately 32.0 to about 35.0 millimeters.

Leaf base-shape: The leaves as seen in a typical canopy generally exhibit equal marginal symmetry relative to the leaf longitudinal axis.

Leaf form: Lanceolate.

Leaf tip form: Acuminate.

Leaf color:

*Upper leaf surface.*—Dark yellow-green, (RHS Yellow-Green Group 146 B).

Leaf texture:

*Upper leaf surface.*—Considered glabrous.

*Lower leaf surface.*—Less glabrous when compared to the upper surface texture.

Leaf color:

*Lower leaf surface.*—Light to medium green, (RHS Yellow-Green Group 146 B).

Leaf venation: Pinnately veined.

Mid-vein:

*Color.*—Considered a light yellow, (RHS Greyed-Yellow Group 160 A) in the early to mid-period of the growing season.

Leaf margins:

*Generally.*—Gently undulating.

*Marginal form.*—Considered finely crenate.

Leaf uniformity: Considered generally uniform.

Leaf petioles:

*Petiole form.*—Considered canaliculated, and having a more pronounced trough when viewed from the dorsal aspect. The petiole margin is considered rounded when viewed from the ventral aspect.

*Leaf petiole size.*—Considered medium-small for the species.

*Leaf petiole length.*—About 5.0 to about 9.0 mm.

*Leaf petiole diameter.*—About 1.5 to about 2.0 mm.

*Leaf petiole color.*—A light, yellow-green, (RHS Yellow-Green Group 145 C).

*Leaf petiole strength.*—Durable for the species until senescence.

*Leaf petiole texture.*—Considered glabrous.

Leaf glands:

*Size.*—Considered small for the species; approximately 1.5 mm. in length; and about 1.0 mm. in height.

*Number.*—Generally one, and less commonly, two glands appear per marginal side. Observations of more than two glands per marginal side are very uncommon.

*Type.*—Leaf glands located at the base of the leaf are predominantly reniform in shape, but smaller in width than typical reniform glands.

*Leaf gland color.*—Considered a medium-dark brown, (RHS Grey-Brown Group 199 A). As the growing season progresses the coloration of the glands typically darkens, and occasionally begins to desiccate by the mid-late season.

Leaf stipules:

*Size.*—Medium for this variety.

*Number.*—Typically 2 per leaf bud, and up to 6 per shoot tip.

*Form.*—Lanceolate in form, and having a serrated marginal edge.

*Color.*—Green, (RHS Green Group 137 C) when young, but graduating to a brown color, (RHS Greyed-Orange Group 164 A) with advancing senescence. The leaf stipules are generally considered to be early deciduous.

FLOWER BUDS

Hardiness: No winter injury (bud death) has been noted during the last several years of observation while the present trees have been growing in the central San Joaquin Valley. The new variety of peach tree has not been intentionally subjected to drought, cold or heat stress, and therefore this information is not available.

Flower bud:

*Size.*—Variable based upon the state of maturity. The flower buds as described, below, were observed approximately 7 days prior to bloom.

Flower bud:

*Length.*—Approximately 17.0 millimeters.

Flower bud:

*Diameter.*—Approximately 10.0 millimeters.

Flower bud surface texture: Pubescent.

Flower bud orientation: Considered appressed, but appearing less so as the floral buds near enfloration.

Bud scale color: Grey-purple (RHS Greyed-Purple 185 C).

FLOWERS

Date of first bloom: Observed on Feb. 27, 2015.

Blooming time: Considered average in relative comparison to other commercial peach cultivars which are grown in the central San Joaquin Valley. The date of full bloom was observed on Mar. 4, 2015. The date of full bloom varies slightly with climatic conditions, and prevailing horticultural practices.

Duration of bloom: Approximately 9 or more days. This particular characteristic often varies slightly with the prevailing climatic conditions.

Flower class: Considered a perfect flower, complete and perigynous.

Flower type: The variety is considered to have a showy-type flower.

Flower size: Considered large for the species. The flower diameter, at full bloom, is approximately 50.0 to 52.0 millimeters.

Bloom quantity: Considered abundant.

Flower bud density: Generally considered moderately dense.

Flower bud frequency: Generally two flower buds appear per node. Occasionally, one flower bud per node is observed.

Petal size: Generally considered large for the species.

*Petal length.*—Approximately 25.0 to 28.0 millimeters.

*Petal width.*—Approximately 17.0 to 20 millimeters.

Petal form: Considered broadly ovate.

Petal count: Nearly always 5.

Petal texture:

*Upper petal surface.*—The upper petal surface exhibits a soft velvety texture.

*Lower petal surface.*—The lower petal surface exhibits a soft velvety texture.

Petal color: Considered a light pink at the popcorn stage, (RHS Red Group 56 A), and darkening with advanced senescence, and the exposure of sunlight, to a medium-dark pink, (RHS Red-Purple 63 C).

Fragrance: Slight.

Petal claw:

*Form.*—The claw is considered ovate in shape, and is generally large in size.

*Length.*—Approximately 18.0 to 11.0 millimeters.

*Width.*—Approximately 8.0 to 10.0 millimeters.

Petal margins: Generally considered variable, from nearly smooth to slightly undulate.

Petal apex: Considered entire. No petal margin has been observed in this variety.

Flower pedicel:

*Length.*—Considered medium with an approximate length of about 3.5 to about 4.5 millimeters.

*Diameter.*—Approximately 2.0 millimeters.

*Color.*—A medium brown, (RHS Grey-Brown Group N199 D) depending upon the pedicel fruit maturity, and timing of the visual observance.

*Surface texture.*—Glabrous.

Floral nectaries:

*Color.*—Considered a medium, saturated orange (RHS Greyed-Orange Group 168 C).

Calyx:

*Surface texture.*—Upper Surface. — A very fine pubescence is present. Lower Surface. — A dull but nearly glabrous surface is observed.

*Calyx color.*—A dull brown red, (RHS Greyed-Red Group 178 B).

Sepals:

*Surface texture.*—The surface has a short, fine pubescent texture.

*Number.*—5 sepals can be observed.

*Sepal size.*—Average.

*Sepal length.*—Approximately 6.5-8.5 millimeters.

*Sepal width.*—Approximately 4.0 to 6.0 millimeters.

*Sepal shape.*—Generally obovate.

*Sepal marginal shape.*—Considered smooth and entire.

*Sepal color.*—A dull red, (RHS Greyed-Red Group 178 A).

Ovary texture: Pubescent.

Anthers:

*Generally.*—Average in size.

*Anther color.*—Orange when viewed dorsally, and prior to dehiscence, (RHS Greyed-Orange Group 168 C).

Pollen production: Pollen is abundant, and has a yellow color, (RHS Yellow-Orange Group 16 B).

Fertility: Self-fertile.

Filaments:

*Size.*—Approximately 13.5 to 16.5 millimeters in length.

*Filament color.*—Considered white to a pinkish-white, (RHS Red-Purple Group 65 D).

Pistil:

*Numbers.*—Usually one, and only rarely more than one.

*Size.*—Considered large.

*Pistil length.*—Approximately 18.0 to about 21.0 millimeters in length including the ovary.

*Pistil color.*—Considered a very pale green, (RHS Yellow-Green Group 154 D).

*Pistil surface texture.*—The variety has a long pubescent pistil.

Stamen position relative to the petals: At flower maturity the stamens grow to be superior to the petals.

Stigma position relative to the anthers: Generally the stigma is superior to the anthers by approximately 1.0-2.0 millimeters.

FRUIT

Maturity when described: Firm ripe condition (shipping ripe).

Date of first picking: Approximately Sep. 18, 2015.

Date of last picking: Sep. 23, 2015. The date of harvest can somewhat vary with the prevailing climatic conditions, crop loads and the current climatic and horticultural practices employed.

Size:

*Generally*.—Considered moderately large, and very uniform.

Average cheek diameter: Approximately 78.0 to about 82.0 millimeters.

Average axial diameter: Approximately 79.0 to about 82.0 millimeters.

Typical weight: Approximately 287.0 grams. This characteristic is highly dependent upon the horticultural practices employed.

Fruit form:

*Generally*.—Considered globose. The fruit is generally uniform in symmetry.

Fruit suture stitching: No stitching exists along the suture line.

Fruit suture:

*Color*.—Generally, the fruit appears blushed to the same degree as the skin, (RHS Greyed-Red Group 179 A).

Ventral surface:

*Form*.—Considered even, and uniform in appearance, when this surface is viewed from the lateral, suturial plane.

Apex:

*Shape*.—Generally rounded, and occasional lobing is observed.

Base:

*Shape*.—Generally smooth.

Stem cavity:

*Form*.—The stem cavity typically has a rounded-circular form which is generally considered uniform. The rounded stem cavity extends, slightly, in the direction of the suture. The average depth of the stem cavity is about 6.0-8.0 mm. The average width of the stem cavity is about 8.0 mm. The average length of the stem cavity, when measured in the suturial plane, is about 25.0-30.0 mm. This measurement varies according to the size of individual fruits which are examined.

Fruit skin:

*Thickness*.—Considered medium in thickness, and tenacious to the flesh.

*Fruit skin surface texture*.—Short, fine and pubescent. The pubescence is moderately abundant.

*Taste*.—Non-astringent.

*Tendency to crack*.—Not observed in the previous years of observation and evaluation.

Fruit skin color:

*Blush color*.—Generally speaking, a dull red blush can be observed on the skin of the fruit (approximately RHS Orange-Red Group N34 A), and is more typically present on the portions of the fruit facing the sunlight. The blush of the fruit typically covers approximately 45%-65% of the fruit skin surface. The percentage of the blush on the fruit skin surface can vary, and is generally dependent upon the fruit's exposure to direct sunlight; specific fruit maturity; and also the prevailing ecological and horticultural conditions under which the fruit was grown.

Ground color: A medium, light yellow, (RHS. Yellow Group 23 B) is observed.

Fruit glossiness: A dull pubescent surface is present.

Fruit stem:

*Size*.—Medium in length, approximately 5.0 to about 8.0 millimeters.

*Fruit diameter*.—Approximately 2.0 to about 3.0 millimeters.

*Fruit stem color*.—Pale yellow-green, (RHS Yellow-Green Group N144 C).

Fruit flesh:

*Ripening*.—Considered even.

*Fruit texture*.—Firm, crunchy, juicy and dense. Considered firm yet non-melting.

*Fruit fibers*.—Present but not prominent.

*Fruit aroma*.—Slight to Moderate.

*Eating quality*.—Considered very good.

*Fruit flavor*.—Considered balanced with sweetness and acidity.

*Juice production*.—Moderate to abundant.

Brix: About 13.0 to 17.0 degrees. This characteristic varies slightly with the number of fruit per tree; the maturity of fruit when harvested; the prevailing horticultural practices employed; and the ambient climatic conditions.

Acidity: Considered medium. Approximately 0.70 titratable acidity is typically, detected. Acid levels assayed from the fruit flesh can vary with the fruit maturity, sunlight exposure, climatic, regional and horticultural influences the tree has been exposed to.

Flesh color: Yellow (RHS Yellow Group 12 A). The flesh may also have pigmentation of red radiating from the stone (RHS Greyed-Red Group 179 A).

STONE

Type: Clingstone.

Size: The stone is generally considered to be medium in size for the variety. The stone size varies with the resulting crop load, and tree vigor.

Stone length: Average, about 36.0 to about 40.0 millimeters.

Stone width: Average, about 24.0 to about 28.0 millimeters.

Stone diameter: Average, about 22.0 to about 24.0 millimeters.

*Stone form*.—Roughly ovoid in shape.

Stone base:

*Shape*.—The base of the stone is considered shortly attenuated.

Stone apex:

*Shape*.—The stone exhibits a slightly acutely-shaped apex.

Stone surface texture: Considered irregularly furrowed toward the apex. Further, more pitting exists in the mid-portion of the stone (laterally), and is more commonly observed toward the base of the stone.

Ridges: Ridging is observed on the stone and is generally more prominent, and usually oriented parallel, and laterally relative at the ventral and dorsal margins of the stone. The folds of the surface ridges appearing on the external margins often end gently along the suture.

Ventral edge: The ventral edge of the stone is generally considered troughed with three substantial grooves that converge apically.

Stone dorsal edge:

*Shape*.—Generally considered even.

Stone color: The color of a mature, dry stone, is generally considered a dull brown, (RHS Greyed-Orange Group 166 B).

Tendency to split: Splitting has only rarely been noted.

Kernel:

*Length*.—Approximately 16.0-19.0 millimeters.

*Width*.—Approximately 13.0-15.0 millimeters.

*Thickness.*—5.0-6.0 millimeters.

*Size.*—The kernel is considered medium in size.

*Form.*—Considered generally ovoid in shape.

*Pellicle.*—Slightly pubescent in appearance.

*Color.*—A dark tan (RHS Greyed-Orange Group 165 B).

Use: The present variety 'Burpeachthirtyeight' is considered to be a peach tree of the late season of maturity, and which produces fruit which are considered to be firm, attractively colored, and which are useful for both local and long distance shipping.

Keeping quality: Appears excellent. The fruit of the present variety has stored well for periods of up to 35 days after harvest at 1.0 degree Celsius.

Shipping quality: Good. The fruit of the new peach tree variety showed minimal bruising of the flesh or skin damage after being subjected to normal harvesting and packing procedures.

Resistance to insects and disease: No particular susceptibilities were noted. The present variety has not been intentionally tested to expose or detect any susceptibilities or resistances to any known plant, fruit diseases, insect, frost, winter injury or other environmental factors.

Although the new variety of peach tree possesses the described characteristics when grown under the ecological conditions prevailing near Fowler, Calif., in the Central part of the San Joaquin Valley of California, it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of peach tree, what we claim is new, and desire to secure by plant Letters Patent is:

1. A new distinct variety of peach tree, substantially as illustrated and described, and which is characterized principally as to novelty by producing an attractively colored yellow fleshed, clingstone peach which is mature for harvesting and shipment approximately September 18 to September 23 under the ecological conditions prevailing in the San Joaquin Valley of central California.

* * * * *